United States Patent [19]

Wood

[11] Patent Number: Plant 6,701

[45] Date of Patent: Mar. 28, 1989

[54] BLUEBERRY — VARIETY PURU

[75] Inventor: Franklin H. Wood, Hamilton, New Zealand

[73] Assignee: Maftech North, Ruakura Agricultural Research Centre, Hamilton, New Zealand

[21] Appl. No.: 102,157

[22] Filed: Sep. 28, 1987

[30] Foreign Application Priority Data

Sep. 29, 1986 [NZ] New Zealand ..... PV 3-50-3

[51] Int. Cl.[4] ..... A01H 5/03

[52] U.S. Cl. ..... Plt./33

[58] Field of Search ..... Plt./33

*Primary Examiner*—Robert E. Bagwill

*Attorney, Agent, or Firm*—Abelman Frayne Rezac & Schwab

[57] ABSTRACT

A blueberry plant bearing high yields of large fruit early in the season.

4 Drawing Sheets

In 1969, seed from a range of blueberry crosses was gifted to Ruakura as a result of an agreement between P. Bates (Ruakura) and A. D. Draper (USDA). The NZ objective was to identify plant material which was more suitable for local conditions. Over a thousand seedlings were initially screened in the first stage evaluation from which forty seedling types were identified as promising. Closer critical examination of these seedlings over several years, resulted in the selection of ten elite types. Seven of these ten seedlkings had Earliblue, Blue-crop parentage and characteristically produced early maturing, high quality fruit. The remainder had Berkeley and Blueray parentage and typically produced later maturing fruit. These elite seedlings were planted out in 1982 in a fully replicated trial to determine their commercial usefulness. Puru, Nui and Reka, three elite Ruakura selections, are chance seedlings arising from Earliblue and Bluecrop crosses. They are the product of careful screening and evaluation which has taken place over many years.

Comparison of Puru and Similar Cultivars

Blueberries are often classified in terms of their seasonability of fruit production. This is a useful parameter which can be used broadly to categorise cultivars as either early, mid or late season producers. The three new Ruakura cultivars are all early producers and in the following reports, will be compared with the earliest available standard cultivars. These cultivars include Earliblue, Collins and Stanley. Also, on the basis of fruit quality, Bluecrop and Darrow have the closest resemblance to these new selections. These varieties will be addressed individually to outline similarities and differences and these are summarised in Table 1.

(a) Earliblue

As a parent of Puru, Earliblue shares many similar traits while also being quite different in others (see Table 4). For example, fruit flavour and colour compare favourably with Puru, while plant vigour and habit is clearly different. Earliblue tends to be less vigorous and produces an open spreading bush while Puru produces a compact, vigorous growth with a resulting denser canopy. Both cultivars produce large, pale blue fruit, although Puru tends to produce more larger fruit throughout the season which leads to a larger average berry size (see Table 2). Puru is also considerably more precocious than Earliblue (Table 1). Depending upon the seasonal climate, Earliblue may crop for extended periods throughout the summer resulting in a drawn-out harvest season. Puru, however, has a very definite peak in its production profile (FIG. 1), with most of the fruit mature before Christmas (pre-Christmas production is a useful tool for quantifying early fruit production).

(b) Collins

This cultivar is very similar to Earliblue and much of the preceding discussion applies equally to Collins. The only obvious difference is that Collins matures a little later than Earliblue and fruit flavour is different from Puru.

(c) Stanley

Stanley also produces early fruit, although later than Puru (FIG. 1, Table 3). However, fruit size is considerably smaller, i.e., an average berry weight of 1.2 gm compared with 2.2 gm for Puru. Stanley has a vigorous upright bush habit which is similar to Puru and also tends to be quite precocious.

(d) Darrow

Of all the highbush cultivars currently available, Darrow would produce fruit that would closely compare with Puru. Fruit size and colour bear close resemblance to Puru, however flavour and seasonality of production are clearly differnt (FIG. 1). Darrow is classified as mid to late with peak production occurring 20–25 days after Puru.

(e) Bluecrop

Also a parent of Puru, Bluecrop has a number of desirable traits that have been passed on to its progeny. This includes scar size, fruit colour, its moderate to large berry size and good bush vigour. Seasonality of production is the main difference between the two with Bluecrop regarded as an early-mid season variety (FIG. 1).

The drawings show flowers, fruit, bush habit, and fruit production data.

DETAILED DESCRIPTION OF PURU

Figure 1:
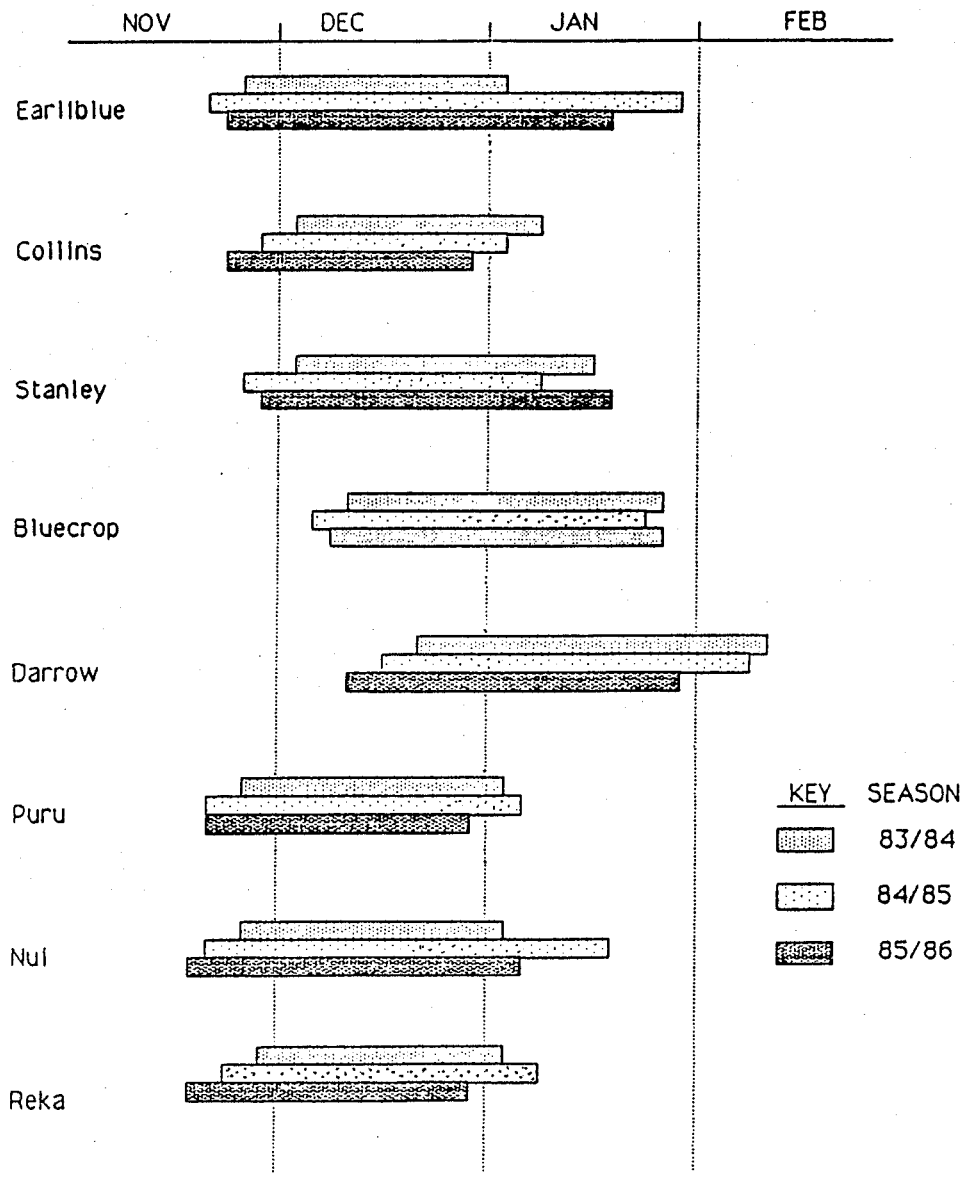
Figure 2:
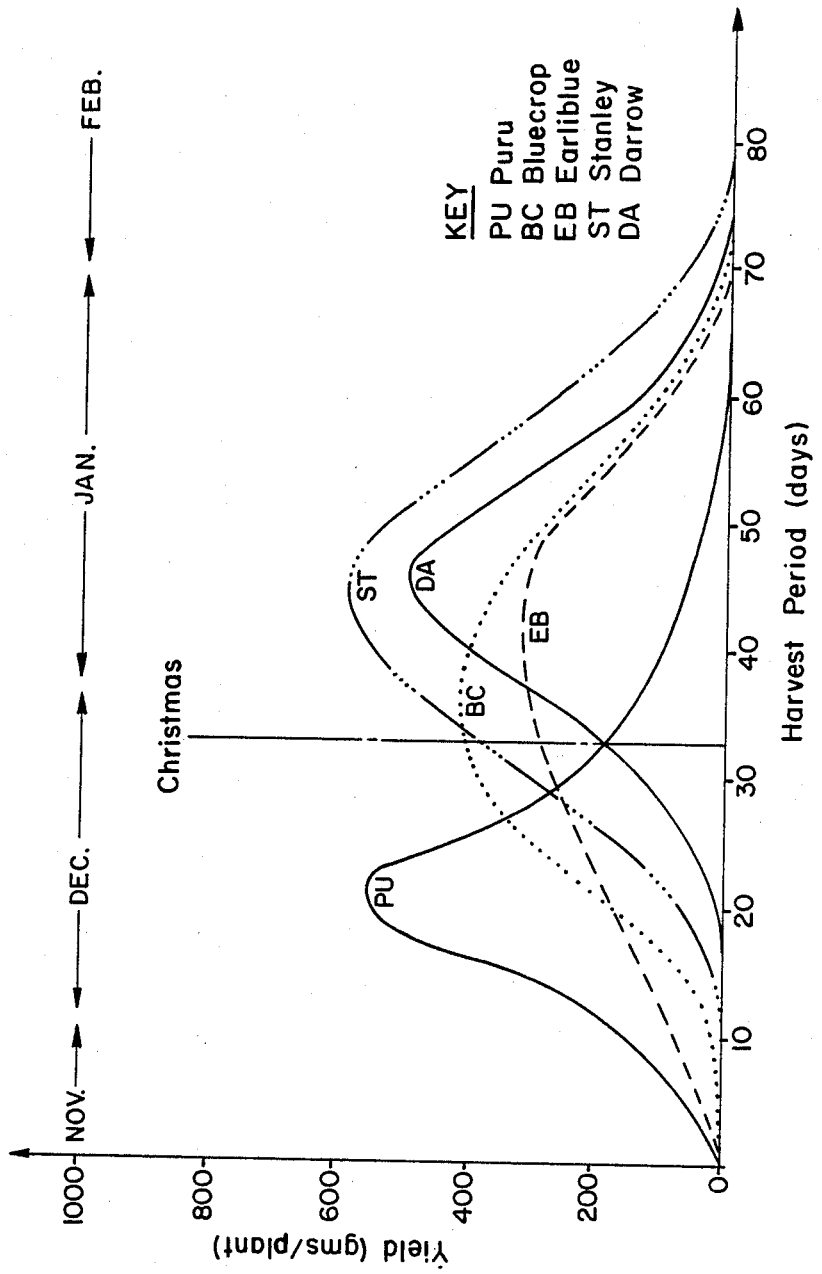

Seedling reference: No. 4.

Flowering habit: White flowers with delicate pink blush red streaks are produced after the leaves in the first or second week of September which is early to mid season in the Southern Hemisphere. Flowers are elongated (cylindraceous). The average corolla length is 8 mm.

Cluster: Small terminal drooping clusters of 4–8 flowers with variable intercluster distances.

Leaves: Deciduous and advanced before flowering. Average length being 71 mm and average width 46 mm. Glossy ovate leaves with deep-set veins and pubescence undersides. The upper surface being light green in summer and the lower surface being pale green.

Stems: Young green canes which yellow with age. Mature canes typified by pubescence layer.

Fruit: Large, pale blue fruit formed in a loose cluster, with pink blush at stem end, produced from late Novembr onwards. The time of ripening being early. In the Southern Hemisphere the fruit production season is late November to early January, mid March to April. The average fruit diameter is 18 mm and the average weight is 2.2 g. The flavour is excellent and the scar is small and dry. Pink/purple stage of maturity longer than normal. The fruit calyx is partially lobed and the fruit shape is substantially flattened. The aroma is medium and the fruit do not tend to drop when ripe. There is medium resistance to cracking.

Bush habit: Compact, upright growth with moderate vigour.

Propagation: Tissue culture difficult. Softwood and hardwood propagation more successful.

TABLE 1

A summary of similarities and differences between Puru and five standard varieties.

| Cultivar | Similarities | Differences* |
|---|---|---|
| Earliblue | flavour<br>early maturing habit<br>berry colour | less bush vigor<br>smaller berry size<br>less precocious<br>larger scar<br>extended harvest |
| Collins | early maturing habit<br>berry colour | less bush vigour<br>smaller berry size<br>less precocious<br>berry firmness<br>larger scar |
| Stanley | early maturing habit<br>bush vigor | smaller berry size<br>less precocious<br>berry flavour<br>berry colour |
| Darrow | berry size<br>berry colour<br>bush vigour | later maturing<br>berry flavour<br>extended harvest<br>larger scar |
| Bluecrop | berry colour<br>scar<br>bush vigour | later maturing<br>smaller berry size |

(*cultivar differences with respect to Puru)

TABLE 2

Fruit production of three new early Ruakura blueberry selections, Puru, Nui and Reka, and five standard varieties.

| | Yields per season (kg/bush) | | | | |
|---|---|---|---|---|---|
| Cultivar | 1 | 2 | 3 | | Year 5 onwards (mean) |
| Earliblue | 0.2 | 0.8 | 1.2 | 1.7 | 2.4 |
| Collins | 0.2 | 0.9 | 1.1 | | 1.6 |
| Stanley | 0.3 | 1.1 | 1.9 | | 3.1 |
| Bluecrop | 0.1 | 0.5 | 1.4 | | 5.8 |
| Darrow | 0.1 | 0.7 | 1.1 | 1.8 | 4.9 |
| Puru | 0.5 | 0.6 | 2.0 | 1.6 | 4.8 |
| Nui | 0.6 | 0.8 | 1.8 | 1.5 | 5.6 |

TABLE 2-continued

Fruit production of three new early Ruakura blueberry selections, Puru, Nui and Reka, and five standard varieties.

| | Yields per season (kg/bush) | | | | |
|---|---|---|---|---|---|
| Cultivar | 1 | 2 | 3 | | Year 5 onwards (mean) |
| Reka | 2.2 | 2.3 | 4.4 | 5.0 | 9.3 |

TABLE 3

Average berry weights of three new early Ruakura selections, Puru, Nui, Reka and five standard varieties.

| Cultivar | Average berry weight (gms) |
|---|---|
| Earliblue | 1.6 |
| Collins | 1.6 |
| Stanley | 1.2 |
| Bluecrop | 1.7 |
| Darrow | 2.0 |
| Puru | 2.2 |
| Nui | 2.1 |
| Reka | 1.6 |

TABLE 4

Pre-Christmas fruit production of three new early varieties, Puru, Nui, Reka and five standard varieties.

| Cultivar | Yield pre-Christmas as a percentage of total production |
|---|---|
| Earliblue | 69 |
| Collins | 82 |
| Stanley | 67 |
| Bluecrop | 55 |
| Darrow | 28 |
| Puru | 91 |
| Nui | 88 |
| Reka | 95 |

TABLE 5

General characteristics of three new early Ruakura selections, Puru, Nui, Reka and five standard varieties.

| Cultivar | Season | Bush Growth Habit | Fruit Size | Fruit Colour | Scar |
|---|---|---|---|---|---|
| Earliblue | v. early | moderate spreading | medium-large | light blue | medium/dry |
| Collins | early | moderate spreading | medium | pale blue | medium/dry |
| Stanley | early | vigorous upright | medium-small | pale blue | medium/dry |
| Bluecrop | mid | vigorous upright | medium-large | pale blue | small/dry |
| Darrow | late | vigorous upright | large | pale blue | medium/wet |
| Nui | v. early | vigorous upright | V. large | pale blue | small/dry |
| Puru | v. early | vigorous upright | large | pale blue | small/dry |
| Reka | v. early | vigorous spreading | medium-large | light blue | small/dry |

Additional Notes (i) Leaf measurements were taken on mature leaves and not at the time of full flowering as the leaves at this stage are still expanding.

(ii) Pubescence on lower leaf surface is confined to central leaf vein only.

(iii) Fruit diameter and weight vary within the season. Early season fruit which is produced on primary whips is much larger and heavier than subsequent fruit produced on secondary and tertiary whips.

(iv) A small autumn crop is produced from mid March onwards. This behaviour is variable and largely depends upon the preceeding dry summer conditions. The small number of fruit produced (in comparison to main crop) tend to be extremely large.

(v) In addition to leaf parameters already stated the leaves of Puru tend to characteristically pucker downwards on maturity, in a similar fashion to that seen in Dixi.

I claim:

1. A new and distinct variety of blueberry, substantially as herein shown and described, characterised particularly by (a) a high percentage of total yield is produced early in the season, (b) large fruit weight, (c) small dry scar tissue.

* * * * *

FIG. 1 Fruit production season of three new early cultivars Puru, Nui and Reka and five standard varieties.

Seasonal yield profile of Puru and four standard varieties (Day 0 is 23 November).

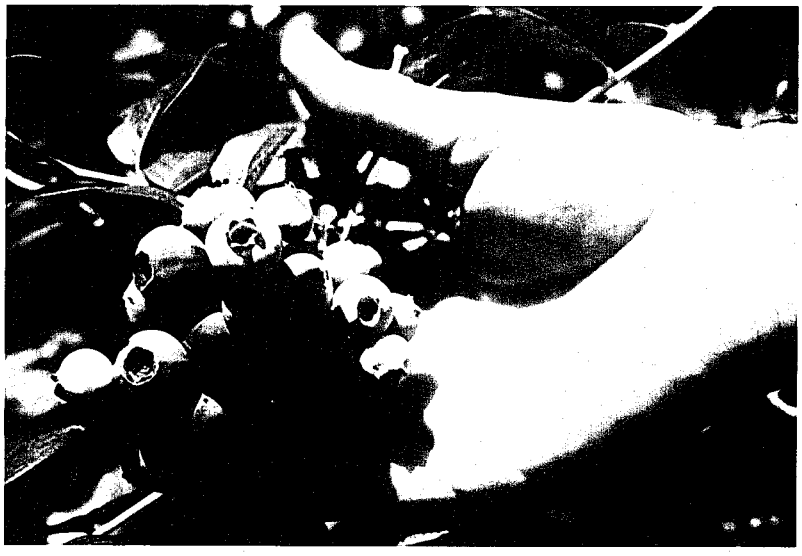
PURU-Fruit Development
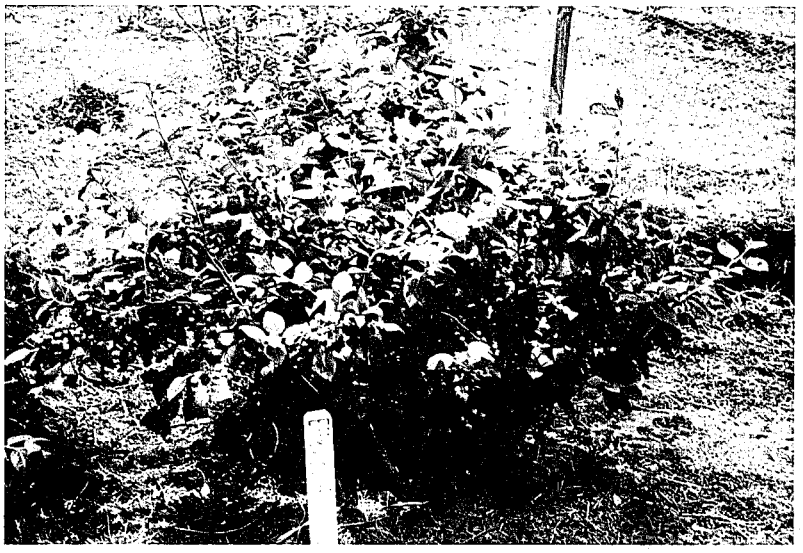
PURU-Bush Habit

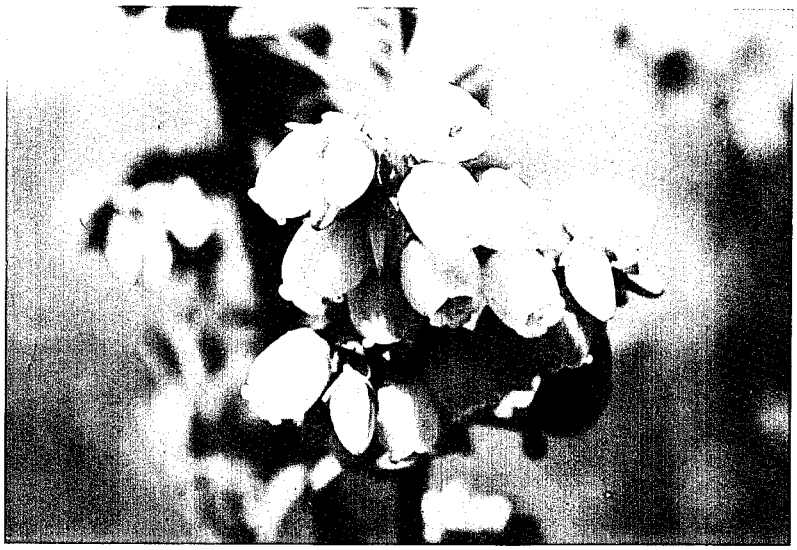
PURU-Floral Development